US 8,500,448 B2

(12) United States Patent
Karlsson et al.

(10) Patent No.: US 8,500,448 B2
(45) Date of Patent: Aug. 6, 2013

(54) DENTAL MODEL, ARTICULATOR AND METHODS FOR PRODUCTION THEREOF

(75) Inventors: Per-Olof Karlsson, Alingsas (SE); Jenny Fäldt, Mölndal (SE); Matts Andersson, Lerum (SE)

(73) Assignee: Nobel Biocare Services AG, Zurich-Flughafen (CH)

( * ) Notice: Subject to any disclaimer, the term of this patent is extended or adjusted under 35 U.S.C. 154(b) by 831 days.

(21) Appl. No.: 12/447,455

(22) PCT Filed: Oct. 18, 2007

(86) PCT No.: PCT/SE2007/000922
§ 371 (c)(1),
(2), (4) Date: Jun. 24, 2009

(87) PCT Pub. No.: WO2008/051141
PCT Pub. Date: May 2, 2008

(65) Prior Publication Data
US 2010/0105002 A1   Apr. 29, 2010

(30) Foreign Application Priority Data
Oct. 27, 2006   (SE) ........................................ 0602273

(51) Int. Cl.
*A61C 11/08* (2006.01)
(52) U.S. Cl.
USPC ............................................................ 433/60
(58) Field of Classification Search
USPC .................. 433/54–67, 24, 34, 74, 201.1, 213
See application file for complete search history.

(56) References Cited

U.S. PATENT DOCUMENTS

| 16,708 A | * | 3/1857 | Blandy | 433/54 |
| 99,598 A | * | 2/1870 | Schaffer | 433/54 |

(Continued)

FOREIGN PATENT DOCUMENTS

| DE | 602015 | 8/1934 |
| DE | 10061088 | 6/2002 |

(Continued)

OTHER PUBLICATIONS

Written Opinion of the International Searching Authority for International application No. PCT/SE2007/000922, mailed on Feb. 8, 2008, in 5 pages.

(Continued)

*Primary Examiner* — Cris L Rodriguez
*Assistant Examiner* — Mirayda A Aponte
(74) *Attorney, Agent, or Firm* — Knobbe, Martens, Olson & Bear, LLP.

(57) ABSTRACT

A model of at least a part of a dental structure, an articulator, and methods of manufacturing such devices are provided. The model and the articulator can be used to approximate the natural movements of a jaw of a patient to facilitate preparation of a dental restoration. The model can include the dental structure, an interface, and at least one void extending from a reference surface of the interface inwardly toward the void. The articulator can include upper and lower portions on which models of upper and lower dental structures can be held. The upper and lower portions of the articulator can be configured to generally maintain a vertical alignment while at least one gap formed between respective first and second alignment components thereof allows horizontal movability of the upper and lower portions relative to each other to test the interfit of the models therebetween.

21 Claims, 11 Drawing Sheets

U.S. PATENT DOCUMENTS

| | | | |
|---|---|---|---|
| 1,587,821 A * | 6/1926 | Darcissac | 433/55 |
| 1,798,518 A * | 3/1931 | Bennett | 433/55 |
| 2,445,639 A * | 7/1948 | Sandhofer | 433/58 |
| 3,059,336 A * | 10/1962 | Windish | 433/70 |
| 3,097,431 A * | 7/1963 | Harris | 433/54 |
| 3,916,524 A * | 11/1975 | Lystager | 433/54 |
| 4,252,523 A * | 2/1981 | Gayso | 433/60 |
| 4,854,868 A * | 8/1989 | Pitre | 433/60 |
| 5,052,928 A | 10/1991 | Andersson | |
| 5,059,758 A | 10/1991 | Andersson | |
| 5,069,622 A | 12/1991 | Rangert et al. | |
| 5,076,785 A | 12/1991 | Tsai | |
| 5,192,173 A | 3/1993 | Andersson et al. | |
| 5,192,472 A | 3/1993 | Andersson | |
| 5,440,496 A | 8/1995 | Andersson et al. | |
| 5,497,336 A | 3/1996 | Andersson et al. | |
| 5,565,152 A | 10/1996 | Odén et al. | |
| 5,587,912 A | 12/1996 | Andersson et al. | |
| 5,607,305 A | 3/1997 | Andersson et al. | |
| 5,652,709 A | 7/1997 | Andersson et al. | |
| 5,725,376 A | 3/1998 | Poirier | |
| 5,733,126 A | 3/1998 | Andersson et al. | |
| 5,752,826 A | 5/1998 | Andreiko | |
| 5,752,828 A | 5/1998 | Andersson et al. | |
| 5,779,833 A * | 7/1998 | Cawley et al. | 156/89.11 |
| 5,800,174 A | 9/1998 | Andersson | |
| 5,880,962 A | 3/1999 | Andersson et al. | |
| 5,938,446 A | 8/1999 | Andersson et al. | |
| 6,062,861 A | 5/2000 | Andersson | |
| 6,212,442 B1 | 4/2001 | Andersson et al. | |
| 6,382,975 B1 | 5/2002 | Poirier | |
| 6,413,085 B1 | 7/2002 | Lee | |
| 6,431,871 B1 | 8/2002 | Luthardt | |
| 6,511,318 B2 | 1/2003 | Kim | |
| 6,579,095 B2 | 6/2003 | Marshall et al. | |
| 6,607,386 B1 | 8/2003 | Andersson et al. | |
| 6,655,962 B1 | 12/2003 | Kennard | |
| 6,671,539 B2 | 12/2003 | Gateno et al. | |
| 6,814,575 B2 | 11/2004 | Poirier | |
| 6,821,123 B2 | 11/2004 | Andersson et al. | |
| 7,089,070 B1 | 8/2006 | Andersson et al. | |
| 7,118,375 B2 | 10/2006 | Durbin et al. | |
| 7,175,435 B2 | 2/2007 | Andersson et al. | |
| 7,220,124 B2 | 5/2007 | Taub et al. | |
| 7,331,786 B2 | 2/2008 | Poirier | |
| 7,333,874 B2 | 2/2008 | Taub et al. | |
| 7,363,239 B1 | 4/2008 | Andersson et al. | |
| 2002/0064759 A1 | 5/2002 | Durbin et al. | |
| 2004/0137406 A1 | 7/2004 | Kennard | |
| 2004/0172150 A1 | 9/2004 | Perot et al. | |
| 2004/0204787 A1 | 10/2004 | Kopelman et al. | |
| 2004/0219490 A1 | 11/2004 | Gartner et al. | |
| 2005/0250075 A1 | 11/2005 | Taub et al. | |
| 2005/0277091 A1 | 12/2005 | Andersson et al. | |
| 2006/0040236 A1 | 2/2006 | Schmitt | |
| 2006/0095242 A1 | 5/2006 | Marshall | |
| 2006/0106484 A1 | 5/2006 | Saliger et al. | |
| 2007/0077537 A1 | 4/2007 | Taub et al. | |
| 2007/0154867 A1 | 7/2007 | Taub et al. | |
| 2007/0190481 A1 | 8/2007 | Schmitt | |
| 2007/0190492 A1 | 8/2007 | Schmitt | |
| 2007/0281284 A1 | 12/2007 | Andersson et al. | |
| 2007/0293748 A1 | 12/2007 | Engvall et al. | |
| 2008/0015727 A1 * | 1/2008 | Dunne et al. | 700/118 |
| 2008/0038692 A1 | 2/2008 | Andersson et al. | |
| 2008/0090211 A1 | 4/2008 | Andersson | |
| 2008/0124681 A1 | 5/2008 | Cha | |
| 2008/0131841 A1 | 6/2008 | Taub et al. | |
| 2008/0193899 A1 | 8/2008 | Karlsson et al. | |

FOREIGN PATENT DOCUMENTS

| | | |
|---|---|---|
| EP | 1957005 A2 | 8/2008 |
| FR | 1438237 | 4/1966 |
| SE | 441333 | 9/1985 |
| WO | WO 2008/051130 A1 | 5/2008 |
| WO | WO 2008/051142 A1 | 5/2008 |

OTHER PUBLICATIONS

International Preliminary Report on Patentability for International application No. PCT/SE2007/000922, issued on Apr. 28, 2009, in 6 pages.

International Search Report received in corresponding PCT Application No. PCT/SE2007/000922, mailed Feb. 8, 2008, 4 pages.

* cited by examiner

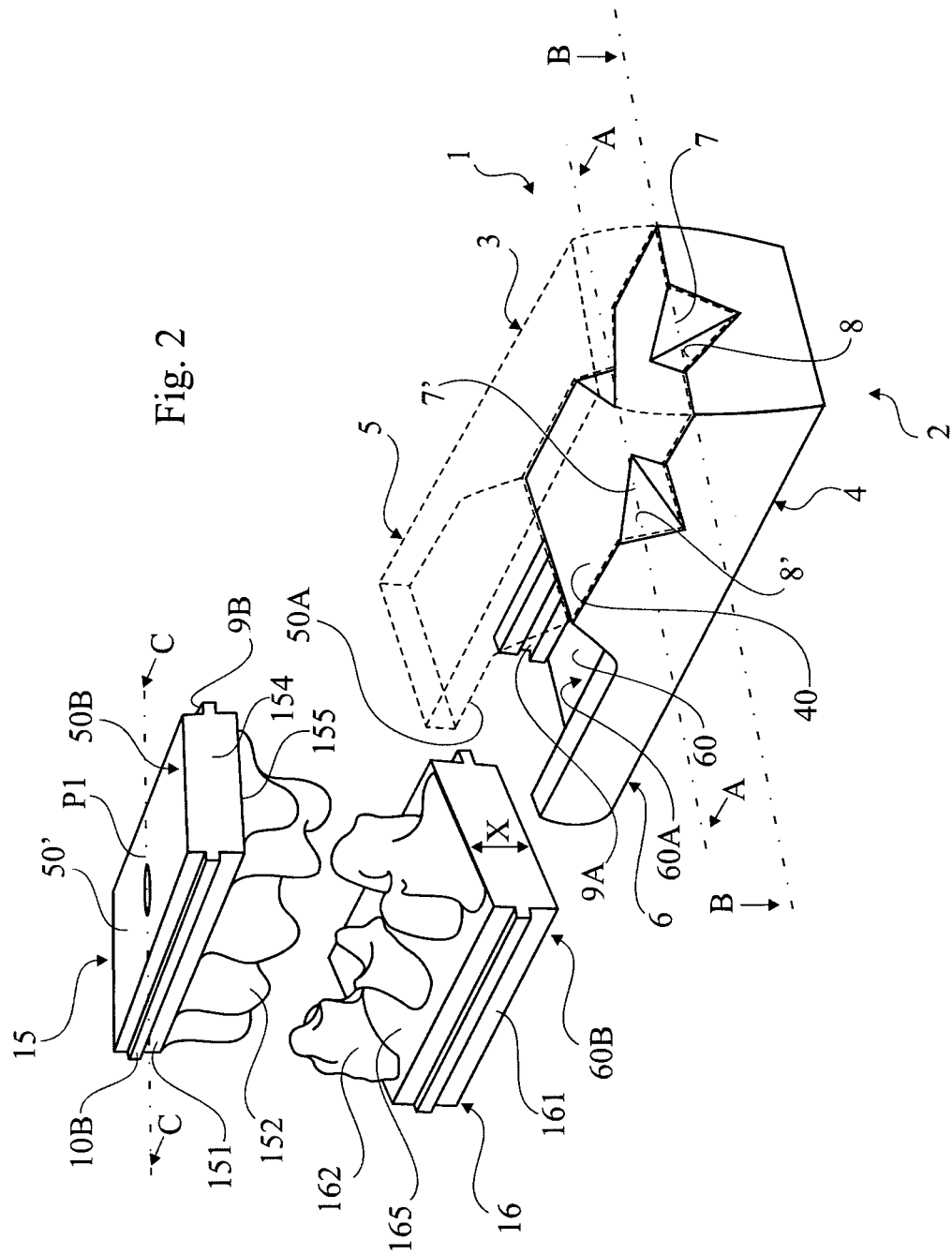

A-A  Fig. 3
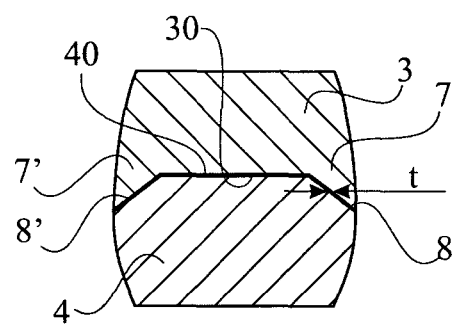
B-B  Fig. 4
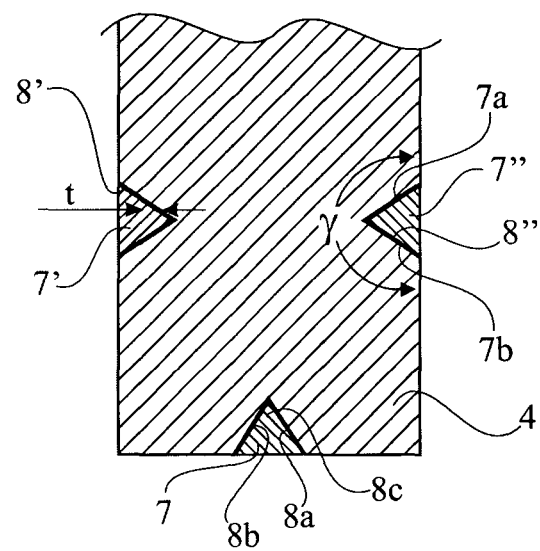

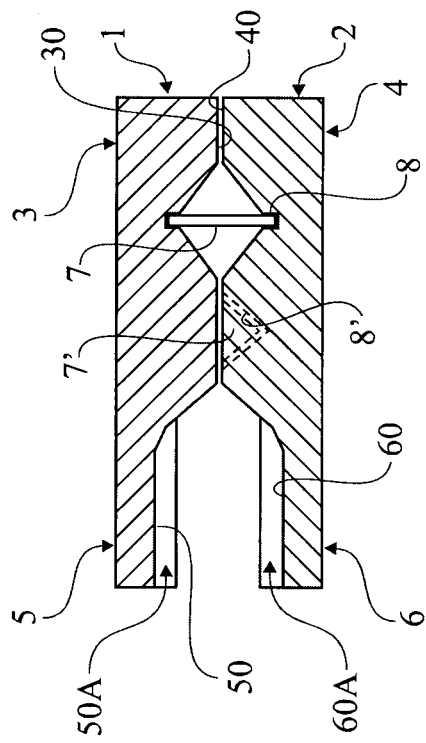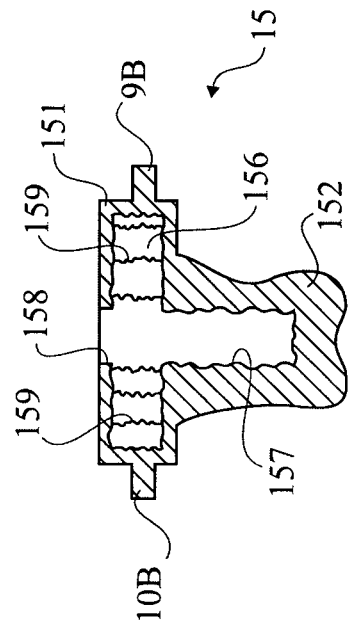

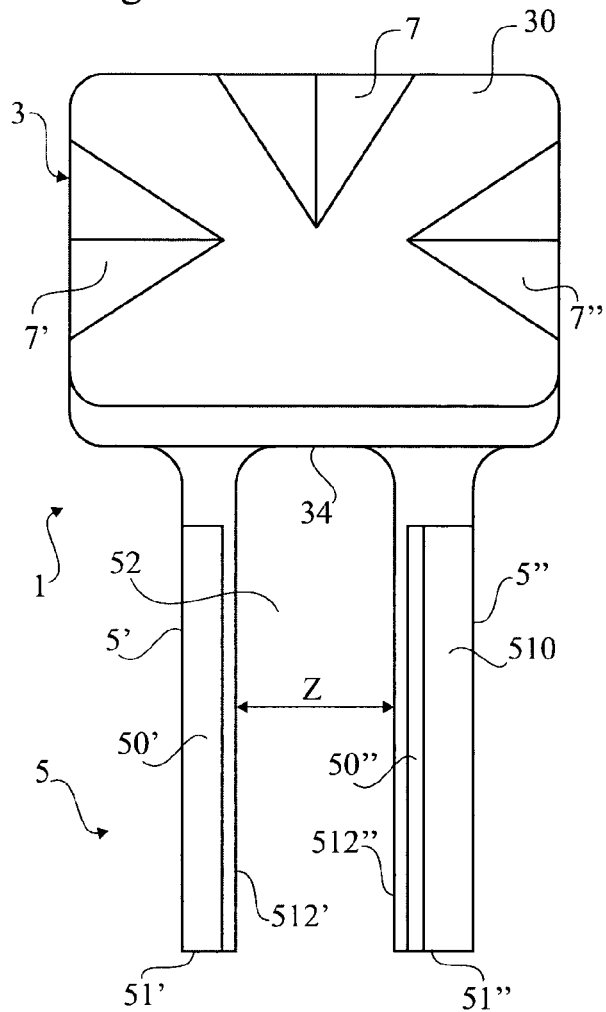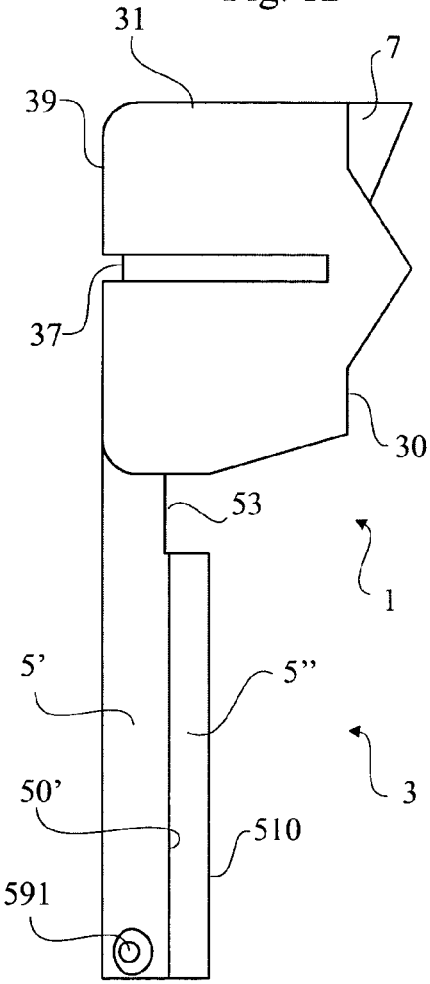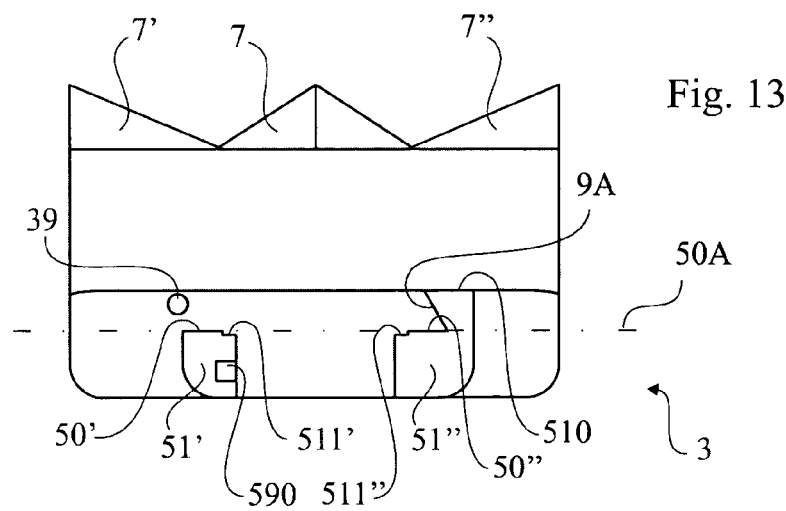

DENTAL MODEL, ARTICULATOR AND METHODS FOR PRODUCTION THEREOF

CROSS-REFERENCE TO RELATED APPLICATIONS

This application is a national stage application under 35 U.S.C. §371 of PCT Application No. PCT/SE2007/000922 designating the United States, filed on Oct. 18, 2007. The PCT Application was published in English, as WO 2008/051141 A1 on May 2, 2008, and claims the benefit of the earlier filing date of Swedish Patent Application No. 0602273-5, filed Oct. 27, 2006. The contents of PCT Application No. PCT/SE2007/000922, including publication WO 2008/051141 A1, and Swedish Patent Application No. 0602273-5, are incorporated herein by reference in their entirety.

BACKGROUND

1. Field of the Inventions

The present application discloses inventions related to a model of at least a part of a dental structure, said model including a dental structure and an interface. It also relates to an articulator, and further to a combination of said articulator and said model. Further, it relates to a method for producing said model and articulator respectively.

2. Description of the Related Art

Production of dental restorations, such as inlays, crowns, bridges, and the like, is based on technologies that have evolved for many decades. The production includes many different steps and involves a number of different specialists and special equipment.

In brief, a traditional manufacturing procedure includes the following steps. First, a dentist makes impressions and an index of the bite of the person who is in need of a dental restoration. The impressions are used to cast an upper half model and an under half model of the bite of the individual. Thereafter the cast models are positioned in an articulator in combination with the index to perform a registration of the bite.

In a subsequent step, grinding is performed to obtain a flat back surface on each model half. Thereafter, pinning and casting is performed to facilitate attachment of a cast base plate to the backside of each model half. After attachment thereof, grinding has to be performed again to adjust the configuration of the base plate to the form of each model half.

In the next step, sectionizing is performed of the model half where the dental restoration is to be inserted, i.e. dividing a portion of that model half into appropriate sections in the area for the dental restoration. Once the sectionizing is finalized, the area for restoration (i.e. the sectionized area of the cast model) is scanned to prepare the framework/coping in a CAD-program. Now the actual manufacturing of the dental restoration may be achieved, by transferring a CAD-file to the production unit.

When the dental restoration is produced, it will be attached to the cast model, i.e. veneering. Thereafter, the dental restoration is adjusted by manual grinding and adaptation in combination with testing it in the articulator.

SUMMARY

As described above, prior art manufacturing procedures require several complex steps before a dental restoration may finally be actually applied into the mouth of a patient. As a consequence, these procedures require not only access to a set of specialized, more or less costly equipment, but also a number of complex activities performed by qualified specialists, which makes it very costly.

In accordance with at least one of the embodiments disclosed herein is the realization that such procedures can be improved by simplifying the procedure and the equipment required. In other words, in accordance with at least one embodiment disclosed herein is the realization that prior art technology involves a complex system that requires considerable investment to facilitate production of dental restorations and also many steps that requires specifically trained staff, which lead to problems concerning cost efficiency, convenience of handling and also possibly quality problems.

An example of such specialized equipment is a pivoting articulator, which is used in the traditional manufacturing procedure discussed above. Such an articulator includes numerous complex details, which of course make it expensive and complicated in use. In brief, it includes a base plate positioned on adjustable feet to be able to level it off. Affixed to the base plate there is a solid support pillar, which at its top has a kind of hinge mechanism for a pivoting lever arm. At its outer end, the lever arm has a specific pointing device that cooperates with a receiving device positioned at the base plate.

In accordance with at least one of the embodiments disclosed herein is the realization that one of the drawbacks associated with such an articulator is that numerous adjustment devices are needed for its function. On top of that, the dental casts have to be attached by plaster to special support plates to be able to fit them into the articulator. Further, a large amount of plaster is needed due to a large distance between the actual transition zone of the dental structure and the interface of the articulator. As is evident, the need of using such equipment makes it hard to achieve cost efficient production.

In DE 395385, DE 602015, DE 419605, U.S. Pat. No. 2,445,639 and U.S. Pat. No. 2,566,131, there is presented a another, simpler articulator that has traditionally been used to test a dental restoration. However, in accordance with at least one of the embodiments disclosed herein is the realization that this articulator presents a design that may not always provide sufficient precision when performing a test therein. Moreover, this ancient technology does not provide sufficient reliability and/or accuracy. Further, this technology requires an extensive use of plaster in the building of the models and support structures for the model, which is undesirable because of several aspects.

According to an embodiments disclosed herein is the realization that the extensive use of plaster is undesirable because plaster is not an easily controllable material; for example, plaster can undergo a relatively large volumetric change dependent on humidity. It should also be noted that the prior art technology described above, which uses a different articulator, also in fact normally requires the use of plaster to build support structures of the dental model. Accordingly, it is realized that this is a common disadvantage concerning the above described prior art technologies. A further disadvantage with the use of plaster is that it is a brittle material.

Accordingly, the present inventions can mitigate, alleviate, and/or eliminate one or more deficiencies, disadvantages or issues in the art, such as the above-identified, singly or in any combination. For example, embodiments disclosed herein can include a model, an articulator, an articulator in combination with a model, and/or a method configured to provide cost-efficient and high-quality production of a dental model. Further, it is contemplated that the model that can be reliably tested in an articulator.

In an embodiment, said articulator comprises an upper portion and a lower portion, said upper portion including a first holding part arranged to hold a model of at least a part of an upper dental structure and including a first positioning device, said lower portion including a second holding part arranged to hold a model of at least a part of a lower dental structure and including a second positioning device, said first and second positioning devices enabling adequate positioning of and movability of said models to test the interfit them between by means of having surfaces of said first and second positioning devices in direct contact with each other and further at least one male/female device having at least one element that protrudes from, or near, one of said surfaces and a corresponding recess near or in the other one of said surfaces.

According to an embodiment, the model can be arranged to present a void and/or said interface is arranged on a body portion that includes a reference surface on one side and a transition zone adjoining it with the dental structure at the opposite side, wherein the distance between said surface and said transition zone is limited, which provides for very small amounts of material needed for the production of the model, compared to prior art methods. The interface can include an engagement arrangement arranged to releasably attach the model to an articulator, which provides for making the articulator being used to be made reusable. The engagement arrangement can be arranged to enable quick lock and release (e.g. a snap fitting), which provides that efficient and convenient handling may be achieved. The engagement arrangement can include a reference surface arranged to enable slide fitting, which provides for the reference surface, including a reference plane, to be used to enable secure and accurate positioning of a model into an articulator. The model can be integrated with an articulator, which provides for exact and durable positioning of the model into the articulator is achieved that may be made extremely strong, e.g., withstanding rough handling during transport. The whole of said model, including said interface and dental structure can be made of a controllably curable material, which provides for high accuracy and quality may be achieved irrespective of variations in temperature and humidity.

According to a further embodiment, an articulator of the kind mentioned above under "technical field" can be provided wherein the male/female device is in the form of at least two, preferably at least three, separate, discrete elements arranged near or in said surfaces and/or wherein the width W of the positioning device adjacent the transition zone between the positioning device and the holding part, is substantially wider than the width w of the holding part, wherein preferably 1,2 w<W<5 w, to provide at least one area at that wall of the positioning device from which the holding part protrudes, such that said area will be reachable across the backside of the articulator, by the finger of a user who holds on to the articulator.

Thanks to this kind of articulator, the production of a dental restoration may be made much more cost efficient than according to prior art. As is evident from the above the articulators used today are complex, including numerous adjustment devices etc., and are therefore expensive devices and relatively complex to handle, whereas an articulator according to embodiments of the inventions forms a surprisingly simple instrument, which both is easy to handle and facilitates cost efficient production. A further important advantage is that it facilitates production of dental models, to be used with the articulator, that requires an extremely small amount of material compared to prior art.

According to further aspects of an articulator according to some embodiments of the inventions, the size and position of said elements and recesses, respectively, are arranged to form a gap between the side walls of each one of said elements and recesses, respectively, when said surfaces are in contact, which provides for a movement of the articulators may be achieved that resembles the natural movements of the jaw of an individual. Further, the holding part can be positioned substantially centrally in relation to the positioning device to provide two reachable surfaces at the front wall of the positioning device, which provides for grip able surfaces are obtained at both sides of the positioning device, at the front surface thereof.

Further advantages of the inventions will become apparent from the following description of different embodiments. It should be emphasized that the term "comprises/comprising" when used in this specification is taken to specify the presence of stated features, integers, steps or components bur does not preclude the presence or addition of one or more other features, integers, steps, components or groups thereof.

BRIEF DESCRIPTION OF THE DRAWINGS

The abovementioned and other features of the inventions disclosed herein are described below with reference to the drawings of the preferred embodiments. The illustrated embodiments are intended to illustrate, but not to limit the inventions. The drawings contain the following figures:

FIG. 2 is a further perspective view of the lower portion of the articulator shown in FIG. 1, further illustrating a dental model to be fitted with the articulator, according to an embodiment.

FIG. 3 is a vertical cross-sectional view of the upper portion and lower portion of the articulator, taken along section line A-A in FIG. 2.

FIG. 4 is a cross-sectional view of the lower portion of the articulator, taken along section line B-B in FIG. 2, illustrating the lower portion of the articulator shown in FIG. 1.

FIG. 7 is a perspective view of an alternative configuration of a male half of an articulator, according to an embodiment.

FIG. 8 is a further perspective view of an alternative configuration of a female part, according to an embodiment.

FIG. 9 is a cross sectional side view of an alternative configuration of an articulator, according to another embodiment.

FIG. 10 is a cross sectional view of a dental model, taken along section line C-C in FIG. 2, according to an embodiment.

FIG. 11 is a front view of a further embodiment of an upper portion or male device of an articulator, according to another embodiment.

FIG. 12 is a side view of the male device of FIG. 11.

FIG. 13 is a view from below of the male device of FIG. 11.

DETAILED DESCRIPTION

Figure 1:
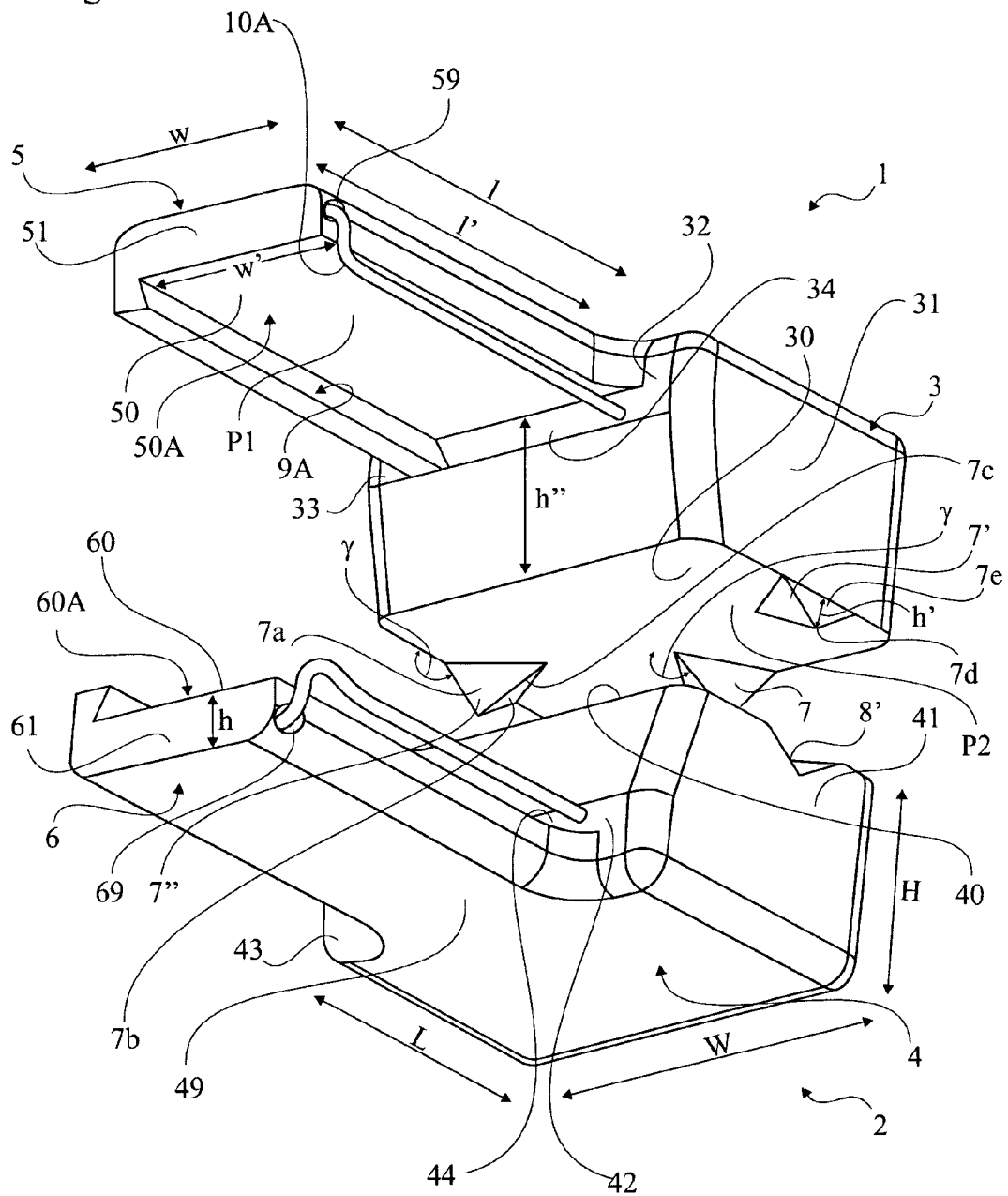
FIG. 1 is a perspective view of an upper portion and a lower portion of an articulator, according to an embodiment of the present inventions.

In FIG. 1 there is shown a perspective view of an articulator according to an embodiment of the present inventions. There is shown an upper portion 1 and a lower portion 2 of said articulator. The upper portion 1 and the lower portion 2 of the articulator are substantially similar in the design, except for their interacting male and a female device respectively, which are described in detail below. As a consequence, both portions 1, 2 will be described jointly in the following. Each portion includes a positioning device 3, 4 and a holding part 5, 6. The holding part 5, 6 includes a support structure 51, 61 in the form of a rigid body having a kind of L-shape in a transversal cross-section. On one side of said holding part 5, 6 there is an interface 50A, 60A arranged to hold a model 15, 16 of at least a part of a dental structure 152, 162 (see FIG. 2). Each interface 50A, 60A includes an engagement arrangement 9A, 10A that enables attachment of the model 15, 16 of a dental structure 152, 162. The dental structure 152, 162 may comprise one or several dental elements. The dental element may comprise at least one of a model of a tooth, a model of a preparation, or a model of artificial dental component. The model of the artificial dental component may e.g. be a model of implant, such as a dental implant, or a model of an abutment.

The engagement arrangement 9A, 10A (in the following merely the upper portion 1 is referred to with reference signs, but the principle is also the same for the lower portion 2) interacts with a reference surface 50, which may be flat, that forms a common reference plane P1 (see FIGS. 2 and 5) together with the backside 50' of the model 15. Hence, the model 15 is intended to rest with its backside 50' in contact with said surface 50, when in correct position.

According to the embodiment shown in FIG. 1, the model 15, 16 is intended to slide into engagement with the articulator 1, 2. This is achieved by arranging the interface 50A, 60A of the holding part 5, 6 with the engagement arrangement 9A, 10A that enables sliding of the model 15 into position and that also retains the model 15 with its backside 50' in contact with the reference surface 50, 60. As shown in some embodiments, the reference plane P1 may be positioned parallel with a central plane P2, which extends between the upper and lower portions 1, 2.

In FIG. 1, it is shown that the engagement arrangement 9A, 10A has a first part 9A at one side of said reference surface 50, in the form of a solid retracting device, here in the form of the recess (which also could be in the form of a ridge, i.e. a vice-versa male/female) that is integral with the support structure 51 of the holding part 5. Extending parallel with said first part 9A of the engagement arrangement, at the other side of the reference surface 50, there is a second part 10A in the form of a rod-like device that is resilient. In the shown example, the resiliency is achieved by using a metal wire (having a diameter of for example about 1-3 mm).

In some embodiments, the second part 10A has appropriate resiliency to securely press the model 15 into contact with the surface of the first part 9A (at the opposite side). The second part 10A may press the model 15 against the reference surface 50. A hole 59 that extends substantially perpendicularly in relation to the main extension of said rod-like device may be provided in the holding part 5. The hole 59 allows the outer end of the second part 10A to move in and out, thereby further increasing flexibility of the rod-like device. As is evident, each model 15, 16 has a corresponding design of its interface 50B, 60B that enables exact position of its backside 50', 60' against the reference surface 50, 60 when put into inter fit with the interface 50A, 60A of the articulator. Thanks to providing sufficient width w' and length l' of the interface 50A, 60A good stability and reliability of an interfit may be achieved.

The interface may have an extension 1' in at least a first direction that is longer than the width of the dental element of said dental structure. This provides e.g. a stable connection to the articulator when connected thereto, whereby fitting possibilities are obtained. However, in other embodiments, the extension in the first direction is shorter than the width of the dental element of the dental structure.

The holding part 5, 6 is integral with the rearward portion 3, 4 of the articulator. The rearward position is also referred to as the positioning device 3, 4. The positioning device 3, 4 forms a substantially bigger body 31, 41 than the support structure 51, 61 of the holding part 5, 6. The reason for this is partly to form a positioning device 3, 4 that has appropriate width W and length L to achieve ergonomically (secure and comfortable) ability to grip and move the upper/lower portions 1, 2 by a human being.

According to an embodiment of the inventions, a further beneficial aspect in this regard is to form the holding part 5, 6 with substantially less width w than the width W of the positioning device. Hereby there are formed areas 32, 33, 42, 43, on each side, at the front of the body 31, 41 of the positioning device 3, 4, i.e. reachable surfaces positioned on the body 31, 41, where the holding part 5, 6 protrudes from the positioning device 3, 4. As can be seen in the figures, this provides for space and corresponding areas 32, 33, 42, 43 that enable a finger of a user to be comfortably positioned from above and below respectively around the positioning device 3, 4, which facilitates safe and comfortable gripping.

According to the embodiment shown in FIG. 1, the width W of the positioning device is in the range of 2-9 mm, preferably 3-5 mm, the length L of the positioning device is in the range of 20-40 mm, preferably 33-42 mm, the width w of the holding part 5, 6 is in the range of 15-40 mm, preferably 20-25 mm, the width w' of the interface 50A, 50 B is in the range of 15-35 mm, preferably 18-23 mm and the length l' of the interface 50A, 50 B is in the range of 28-60 mm, preferably 34-40 mm. Further, the height H of the positioning device 3, 4 is substantially larger than the height h of the holding part 5, 6. Preferably, the height H of the positioning device 3, 4 is in the range 11-25 mm, more preferred 15-21 mm and the height h of the holding part 4, 5 is in the range of 2-9 mm, preferably 3-5 mm. The reason to this design will be explained in more detail below.

The positioning devices 3, 4 are arranged to be in direct contact with each other during use, by means of positioning surfaces 30, 40. In the FIG. 1 embodiment, the surfaces 30, 40 are in a form of flat surfaces. Within these surfaces 30, 40, there are arranged male/female devices 7, 7', 7", 8, 8', 8". As shown in the figure the upper portion 1 (or vice versa) is arranged with the male devices in the form of protruding elements 7, 7', 7" and the lower portion 2 being arranged with corresponding female devices in the form of corresponding recesses 8, 8', 8". In the following, merely the male devices (i.e. that protrude) will be described more in detail, since the female devices are complementary formed.

As also can be seen from FIG. 1, the male devices are in the form of three separate discrete elements that protrude from the positioning surface 30, which forms one side of said central reference plane P2 of the articulator 1, which reference plane P2 is preferably positioned (at least substantially) parallel with the central, horizontal plane of the bite of the individual. Each discrete element 7, 7', 7", 8, 8', 8" has a shape that will enable desired movability of the holding parts 5, 6 in relation to each other, which movability resemble the natural movements of the jaw of the individual that is in need of a dental restoration.

As is evident from the latter the exact form of the protruding elements 7, 7', 7" may differ from one articulator to another (or the elements may be made exchangeable having different configurations, i.e. a set of exchangeable elements for each portion 1, 2) due to the fact that different individuals have different patterns of movement of the jaw. In FIG. 1, it is shown that these elements 7, 7', 7" are triangularly shaped. Each one of the elements includes a first 7a and a second 7b triangularly shaped surface that is inclined and which in their inter junction form an inclined ridge 7c that terminates in a sharp point 7d at a distance h' above the positioning surface 30. The measure h' is preferable in the range of 2.5-5 mm, for example about 3.5-4 mm. The inclination of each surface 7a, 7b is chosen such that the angle γ that is formed between the positioning surface 30 and each ridge 7c form substantially the same angle γ in the range of 143-152°, preferably about 145-149°.

The angle γ may vary in order to provide for a movement of the articulator that enables as close realistic movability as possible, depending on the constitution of the jaw of different individuals. Hence, it may be preferable to have a number of articulators having exactly the same kind of configuration except for the form of the male/female devices, to easily provide different patterns of movement. Needless to say, the form of the female device is beneficially adapted to exactly correspond to the form of the male device. However, it is foreseen that to achieve better simulation of the movement of the jaw there may be situations where some kind of deviation of the form of the male and female device may be beneficial.

As mentioned above the angle γ of each ridge 7c is preferably substantially the same, and presenting surfaces 7a, 7b, enabling sliding movements, extending between the ridges 7c. In the embodiment shown in FIG. 1, the ridges 7c are positioned such that they extend in parallel and perpendicular planes respectively in relation to the extension of the upper portion 1. Two of the protruding elements 7', 7" are positioned symmetrically adjacent the sidewalls of the body 31 of the positioning device 3, such that the side wall 7e of each of said discrete elements 7', 7" are coplanar (i.e. substantially vertical) with the side walls of the holding part 3. Hence, the ridges 7c delimiting these side walls 7e will extend in a plane parallel with the length direction of the upper portion 1. Both of these latter ridges 7c of each discrete element 7', 7" will present the same inclination. In the preferred mode, also the third ridge 7c, that extends in the plane perpendicular to the length extension of the upper portion 1, presents the same inclination.

As is clear from the figures, the two discrete elements 7', 7" that are symmetrically positioned will have their respective perpendicularly extending ridges 7c, extending in the same plane, i.e. a plane that is perpendicular in relation to the length extension of the upper portion. Tests have shown that the use of γ of about 147° provides a realistic movability for most applications. Also, the third protruding element 7 can present a corresponding configuration as has been described above, but having its vertical side wall coplanar with the rear wall of the body 31 of the positioning device 3.

In the embodiment shown in FIG. 1, the holding part 5 and the positioning device 3 have back surfaces 39, 49, (see also FIG. 5) that are positioned substantially in the same plane, forming a common substantially flat surface. Accordingly, the reference surface 50 of the holding part 5 will be positioned much closer to the back surface 39 than the reference surface 30 of the positioning device 3. Hence, there exists a distance h" between the plane P2 including the positioning surface 30 and the plane P1 including the reference surface 50 of the holding part 5. The distance h" between these planes P1, P2 is important due to the fact that it will enable sufficient space for attaching the model 15 within the first part 1 at an accurate and appropriate distance in relation to the model 16 that is positioned in the second part 2. In a preferred embodiment, this distance h" is in the range of 8-20 mm, preferably 10-15 mm.

Thanks to the use of embodiments according to the inventions, that distance h" may be kept relatively narrow, which in turn leads to the fact that considerable savings in material may be achieved in the production of each dental model 15, 16. In some applications, even further cost savings may be achieved by, reducing the distance h" in relation to one of the portions 1, 2, i.e. that portion carrying the occlusive dental model, since the model of that portion must not present any soft tissue and can therefore be made shorter. Accordingly, in such an embodiment the plane P2 will not be positioned symmetrically between the reference planes P1, P3 of the interfaces 50A, 60B. This embodiment may e.g. be useful if either the model of the upper jaw or the model of the lower jaw requires more space than half the distance between the reference planes P1, P3 of the interfaces 50A, 50B.

In FIG. 2, there is shown an articulator that essentially corresponds to the design of the articulator described in conjunction with FIG. 1. A minor difference lies in the shape of the engagement arrangement 9A, 10A, since according to the embodiments shown in FIG. 2 both parts of the holding arrangement 9A, 10A are formed integrally with the body 51, 61 of the holding part 5, 6 of the articulator. As is evident, the dental models 15, 16 will then have a corresponding engagement arrangement 9B, 10B as part of their interface 50B. The exact shape of the interfit of the interfaces 50A, 50B, 60A, 60B may vary, e.g. presenting varying complementary shapes of a recess and protrusion respectively, and also have the interfit arranged vice versa, i.e. the model arranged with the exterior part of the interface (e.g. common in connection with a model forming the whole bite). Regarding other aspects, the dental models 15, 16 intended for the articulator in FIG. 1 are more or less the same, as is evident for the skilled person within the field.

In FIG. 2, it is indicated that the back surface 50' of the dental model 15 forms the plane P1 that is common with the surface 50 of the articulator when the dental model 15 is inserted into position within the articulator. Accordingly, the back surface 50' of the model 15 is in contact with the reference surface 50. Furthermore, FIG. 2 shows that there is a substantially vertical surface 154, at a first side wall, that will enable exact positioning of the model 15, lengthwise, by positioning said surface 154 in contact with the corresponding opposing surface 34 of the articulator 1 (see FIG. 1). The engagement arrangement 9B, 10B, the reference plane 50' and the vertical surface 154 are integral with, and positioned at the periphery of, the support body 151 of the model 15.

Moreover, FIG. 2 shows that the side where the model of the dental structure 152, 162 of an individual is arranged, faces in the opposite direction in relation to the reference surface 50', 60'. The transition zone 155, 165 between the dental structure 152, 162 and the interface 150B, 160B may thanks to the embodiments of the inventions be positioned very close to the reference surface 50', 60', i.e. providing a limited thickness X in the range of 2-10 mm, preferably 3-5 mm. The width w' and the length l' of the model 15, 16, respectively, according to the shown embodiment is the same as for the interface 50B, 60B, and then of course substantially the same as that of the interface 50A, 50B of the articulator, (see FIG. 1)

Further FIG. 2 indicates that there may be a hole 158 centrally positioned within the reference surface 50', 60'. As is more clearly shown in FIG. 10 (cross section C-C of the upper dental model of FIG. 2), the dental model 15, 16 may form a hollow body 151, 152 presenting a void 156 that communicates with the opening 158, which provides for substantial saving of material, e.g. about 50% compared to a solid body 151, 152. It is also presented that the inner walls 157 may have an uneven surface (forming ridges), which may be beneficial regarding strength. To even further enhance the strength of the model 15 the polymeric material may be supplied during production in a manner to form a support structure 159 extending across the void 156. The support structure may e.g. form a framework, such as one or several bridges.

According to some embodiments of the inventions, the dental model 15, 16 is produced by free form fabrication (FFF), which provides for synergies. Especially in conjunction with the latter kind of embodiment, this provides for many synergies, since in such an embodiment considerable cost may be saved, as a consequence of using less of expensive material and less time in the expensive FFF production equipment. On top of that, it leads to less production complications, e.g. less shrinking and quicker solidification. The preferred methodology providing a beneficial way of producing these models 15, 16 by free form fabrication is explained more in detail in another application (i.e. having the title: "Method and system for obtaining data for a dental component and a physical dental model") filed by the same applicant, which has been filed exactly the same day as the present application and which is hereby introduced by way of reference.

In brief, the FFF methodology makes use of storing a digital record of the design of the articulator, and especially the reference plane P2 (i.e. the common plane for the positioning surfaces 30, 40) and each interface 50A, 60A (defining the reference planes P1 and P3 in some embodiments) to thereby enable rational production by free form technology of the interfaces 50B, 60B of the models 15, 16. In some cases, the upper and lower portion 1, 2, respectively, is produced as an integral piece together with the model 15, 16, and thereby making also the reference plane 50A, 60A of the articulator portions 1, 2 integral with the rest.

Hence, this new methodology in a surprisingly efficient manner provides for secure and reliable registration of the dental structure of an individual and also the transfer of said digital registration into a production system that enables accurate and cost efficient production of the dental model in a controllably curable material (e.g. by means of SLA (Stereo Lithography Apparatus and then e.g. using a photopolymer resin material), SLS (and then use a laser fuseable powder), 3D printing, FFF by masking, precision casting, vacuum forming etc.), thereby reducing considerable amount of costly manual adaptation otherwise needed, if using prior art methods. However, it also facilitates considerable savings of material in the actual production, since with this new methodology the amount of material used for the actual model of the dental restoration may be efficiently minimized, e.g. considerably reducing waste.

In brief, the new method will be based on the following steps. First, a special tray is used to obtain an impression of the bite from the individual in need of dental restoration. The tray includes devices that allow for digital registration by a scanner of the exact positioning of the tray in relation to the bite. In the next step, the impression is scanned and the exact positioning of the bite registered by means of the scanner, in a digital data file (e.g. a STL-file).

Thereafter, a CAD design program (preferably Procera®) is used to digitally build the restoration and digitally storing said restoration. Thereafter, the actual production of the model 15, 16 is produced, and also the dental restoration, whereby the interface 50B, 60B of the model halves are adapted to fit into an upper and lower part 1, 2 of an articulator that is to be used, i.e. using the registered measurements from the scanning to exactly position the interfaces 50B, 60B of the dental models 15, 16 in relation to the interface 50A, 60A of the articulator.

Thereafter, the dental models 15, 16 are secured in the articulator and subsequently the dental restoration (not shown) fitted into its intended position. Now the veneering will be performed, i.e. positioning the dental restoration into position on its model half 15, 16 (or possibly both model halves if more than one restoration) and in this connection using the articulators to simulate the movement of the jaw of the individual, for fit checking. As already mentioned above, the chosen articulator may beneficially be adapted to have male/female devices 7, 8 that are shaped to (more or less) exactly correspond to the movement of the jaw of the individual. Accordingly, a very exact veneering may be achieved and therefore the final adaptation of the restoration, i.e. grinding, may be achieved with high quality.

As a consequence of this new method, very few production steps are needed, compared to a prior art technology, to produce a dental restoration ready for final affixation in the mouth of the patient. In fact, with the new technology, many more dentists will be able to assist in applying dental restorations, since all needed adaptations and production steps regarding the dental restoration and model halves may be performed in a distributed manner, i.e. performing different steps at different (possibly distant) locations, since based on the digital scanning recorded from the bite that is supplied by the dentist, the digital information needed in different steps is easily transferred electronically. Accordingly, the dentist merely needs to have access to the tray for making the impression. All other operations may be performed by more or less "centralized" laboratories and production sites, involving an optimized number of specially trained people, which thanks to the high level of computerization may produce the dental restorations in an extremely cost efficient manner. A further major advantage is that the use of plaster may be totally eliminated.

In FIG. 3 there is shown a cross-sectional view of the articulators shown in FIG. 2 along a vertical plane that passes through the male/female devices 7', 7", 8', 8" that are positioned near the centre of the positioning surfaces 30, 40. The design according to the preferred embodiment is such that no gap t is formed between the male device 7 and the female device 8. However, a minor gap t may sometimes be accepted. Hence, according to a preferred embodiment said gap t should be kept within tight limits, i.e. 0-1 mm, preferably less than 0.5 mm.

In FIG. 4, there is shown a cross-sectional horizontal view of the articulator along B-B in FIG. 2, wherein the cross-sectional plane is positioned horizontally and (as seen in FIG. 2) below the common plane P2 of the contacting surfaces 30, 40 of the articulator, but parallel therewith. As is evident from FIG. 4, due to using discrete elements 7, 7', 7", 8, 8', 8" the gap t is continuous in each horizontal plane that crosses a male/female device, between the opposing surfaces 7a, 7b/8a, 8b of the protruding devices 7, 7', 7", and recesses 8, 8', 8" respectively. As shown in the figure, the gap t will be continuous all the way, corresponding to an angle α of at least 180° (360° if positioned inside of the side edge of the contacting surfaces), in each horizontal cross-sectional plane including both the male and female device.

Figure 5:
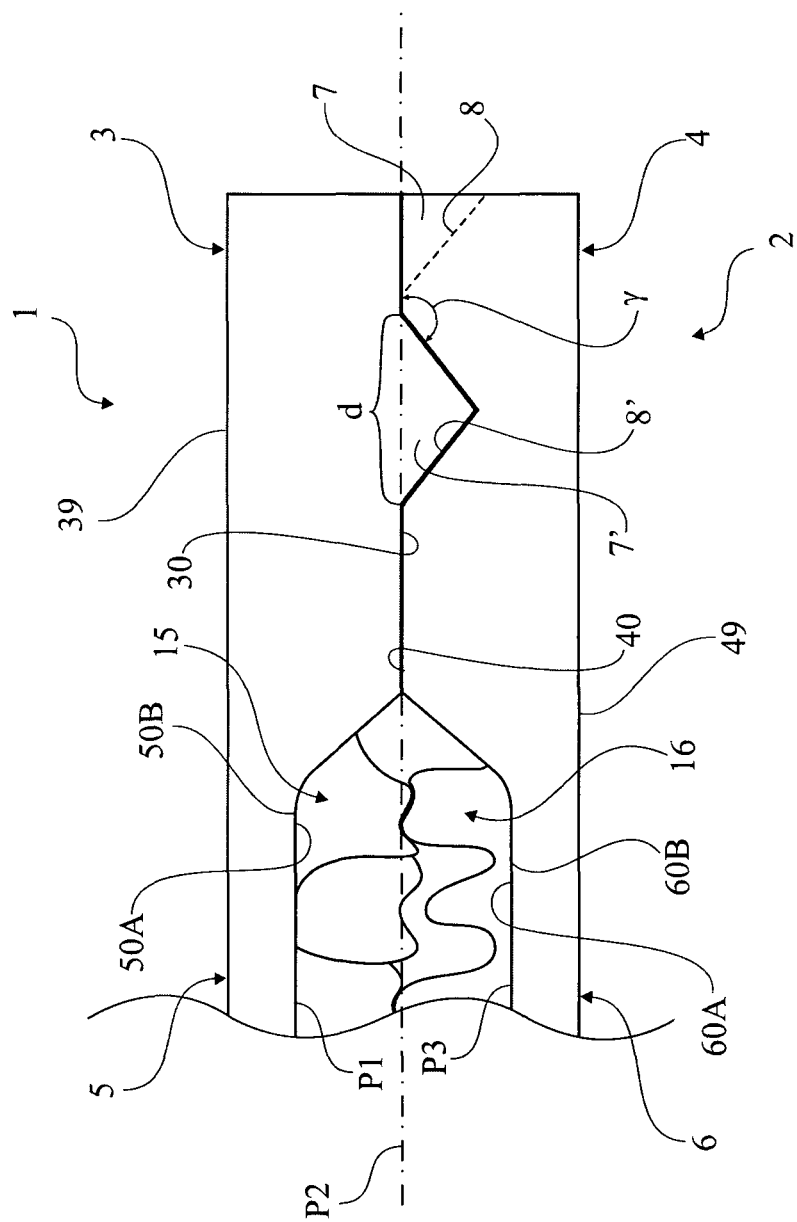
FIG. 5 is a side view of the articulator and model shown in FIG. 2, in an assembled mode, according to an embodiment.

In FIG. 5, there is shown a side view of an articulator comprising dental models 15, 16 according to an embodiments of the inventions. Most features of the embodiment shown in FIG. 5 are the same as described above. An important difference is that according to the embodiment shown in FIG. 5, the articulator and dental models 15, 16 are integral, i.e. fixedly attached to each other. In one embodiment, this is achieved by producing both the articulator and the model halves in the very same production step, preferably by the use of FFF-technology. However, it is foreseen that different production techniques may be used for the articulator and the dental models 15, 16 respectively, e.g. FFF-technology for the dental models 15, 16 and form molding of the upper and lower portion 1, 2, respectively, of the articulator, wherein possibly different sets of male/female devices may be used during the form molding to achieve different movability of the articulators. In such an embodiment, the dental models 15, 16 and its respective portion 1, 2 may be fixedly attached to each other by any appropriate attachment method, e.g. the use of adhesives, welding, screws, etc.

Figure 6:
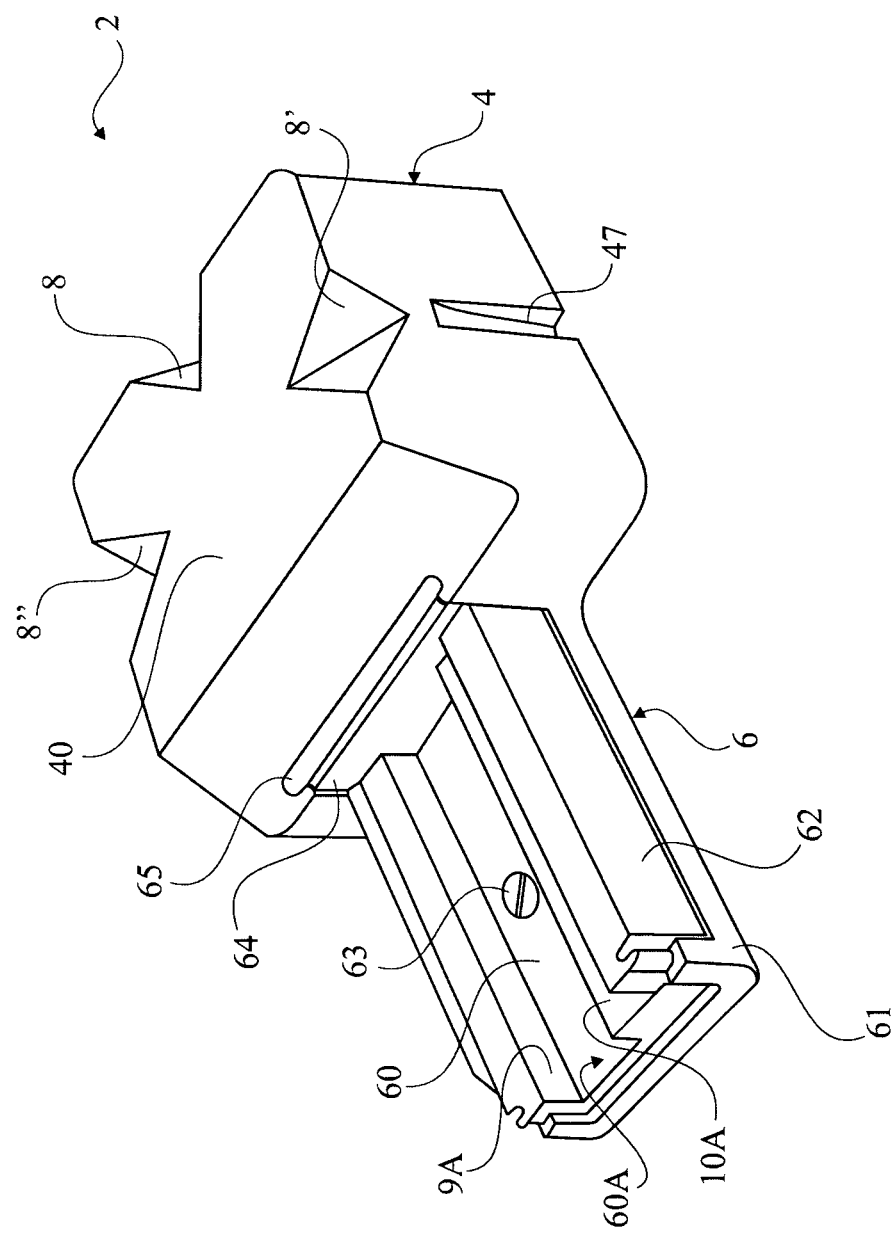
FIG. 6 is a perspective view of a modified embodiment of a lower portion of an articulator.

In FIG. 6, there is shown a lower portion 2 of an articulator, which in most aspects is designed in accordance with what is shown and described in relation to FIGS. 1-4. The modification of the articulator shown in FIG. 6 resides in making the interface 60A adjustable, e.g. to be able to adjust the distance h between the backside 49 of the articulator and the reference plane P3 of the interface 60A. This is achieved by arranging an adjustable body 62, that is separate and adjustable in relation to the body 61 of the holding part 6. In the shown embodiment, this is achieved by creating a recess within the body 61 of the holding part 6 and providing the adjustable body 62 with an outer configuration that corresponds to the configuration of the recess. As can be seen in FIG. 6, this is preferably performed in such a manner that the movement of the adjustable body 62 is totally controlled, i.e. by the use of interfitting shapes that eliminate undesired rocking or tilting of the body 62 in relation to the holding part 6. In the embodiment shown, a screw 63 is used to perform the desired adjustment, i.e. rotation of the screw will move the adjustable body 62 in relation to the holding part 6.

In FIGS. 7, 8 and 9, there are shown different modifications of the male/female devices that may be used to achieve the desired movability between the upper and the lower portion 1, 2 of the articulator (in the figures merely the female portion 2 of the positioning device 4 is shown). In FIG. 8, it is shown that three discrete elements 8, 8', 8" are used. One discrete element 8', 8" is positioned at the centre of each one of the sidewalls of the body 41 of the positioning device 4 (as is also the case with the embodiment shown in FIGS. 1-6). The third discrete element 8 is positioned at the centre of the rear wall of the body of the positioning device 4. The shape of each element 8, 8', 8" is in the form of semispherical indentations. Hence, the side walls of the indentations are curved and positioned such that the centre line of the radius of the sphere, in the horizontal plane, substantially coincides with the side walls of the positioning device 4.

In FIG. 8, a similar figure as in FIG. 7 is shown, but with the difference that each discrete element is positioned totally within the surface 40 of the positioning device 4 and presents a shape in the form of a truncated cone. Accordingly, this embodiment provides a gap t that is continuous 360° in the horizontal plane.

In FIG. 9 there is shown an embodiment, wherein the two male/female devices along the side edges of the articulator are exactly the same as shown in FIGS. 1 and 2, but where the "middle wise" positioned (seen transversely) male/female devices are in the form of a resilient pin that is fixed to the upper portion 1 with its upper end and that has its lower end insertable into a corresponding hole 8 in the lower portion 2 of the articulator. Thanks to the resiliency of the pin, the different halves of the articulator may be moved in a desired manner.

In FIGS. 11, 12 and 13, there is shown a further embodiment of a male device 1 of an articulator according to the inventions. Most of the aspects of this embodiment are similar to or exactly the same as what has been described above in relation to other embodiments. As a consequence, the same reference numbers have been used for many details shown in this further embodiment indicating that they are exactly the same or at least similar or having the same function. The most distinguishing difference is that the male device shown in FIGS. 11-13 is provided with a holding part 5 that has been divided into two legs 5', 5", to thereby provide an open space 52 in between the two legs 5', 5".

An advantage with providing such an open space 52 is that it makes it possible to use the method in connection with dental models 15, 16 arranged with protruding dental elements, e.g. dental implants or a dental implant replicas, extending into (or at least partly into) the open space 52, such that these protruding parts may freely protrude into or through the open space 52 of the holding part 5. Moreover, it also provides some saving of material. The distance Z between the innermost sides of the legs 5', 5", defining the with of the open space 52 is according to the shown example about 12 mm. It is evident that this distance Z may be chosen within a wide range, e.g. 5 mm-50 mm, depending on different needs in different situations/applications.

As shown, preferably the two legs 5', 5" are differently shaped. A first leg 5' is merely provided with one support surface 50', positioned in the sliding plane 50A of the articulator. Further, this leg 5' is also provided with an indentation or groove 590 adapted to support a front end of the retaining device 10A (see FIG. 16 or 17). Moreover, as is shown in FIG. 12, the first leg 5' is arranged with a bore 591 intended to retain a part of the front portion of the retaining device 10A. The front end of the retaining device 10A is folded to be hidden/retained within the groove 590, whereby also a secure fixing of the retaining device is obtained (not shown).

The second leg 5" is also arranged with a support surface 50" within the sliding plane 50A. Further (as also presented in the embodiment shown in FIG. 1), the second leg 5" is provided with an inclined engagement surface 9A, having the same function as already defined above, in connection with FIG. 1. Further, as is clear from both FIGS. 12 and 13, the engagement surface 9A is formed in an uppermost positioned portion of the second leg 5", having an upper surface 510 that terminates at a distance above the sliding plane 50A.

In FIGS. 11 and 12, it is shown that the supporting surfaces 50', 50" and engagement surface 9A do extend a limited distance from the outer ends 51', 51" of the legs along the legs, such that there is a gap between the sidewall 34 of the rearward portion 3 and said surfaces 50', 50", 9A forming a lowermost upwardly facing surface 53. Further FIGS. 12 and 13, make it clear that the lowermost upwardly facing surface 53 of each leg 5', 5" is positioned at a level that is below the sliding plane 50A.

Figure 14:
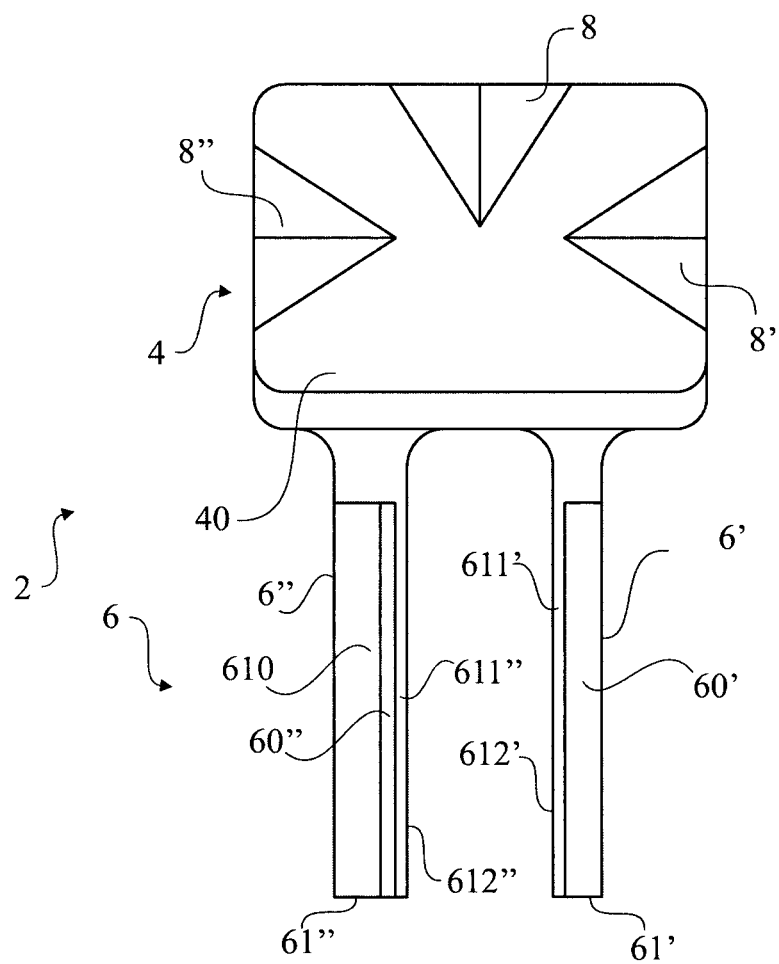
FIG. 14 is a front view of a lower portion or female device, intended to cooperate with an upper portion or male device of the embodiment shown in FIGS. 11-13, according to another embodiment.
Figure 16:
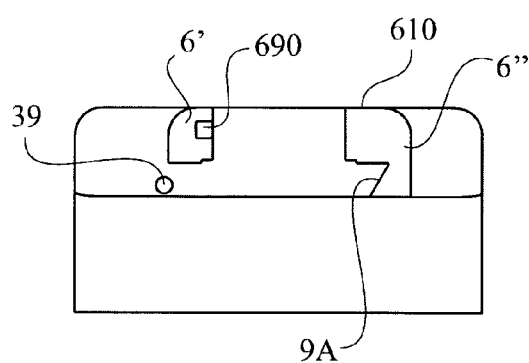
FIG. 16 is a view from below of the device shown in FIG. 14.
Figure 15:
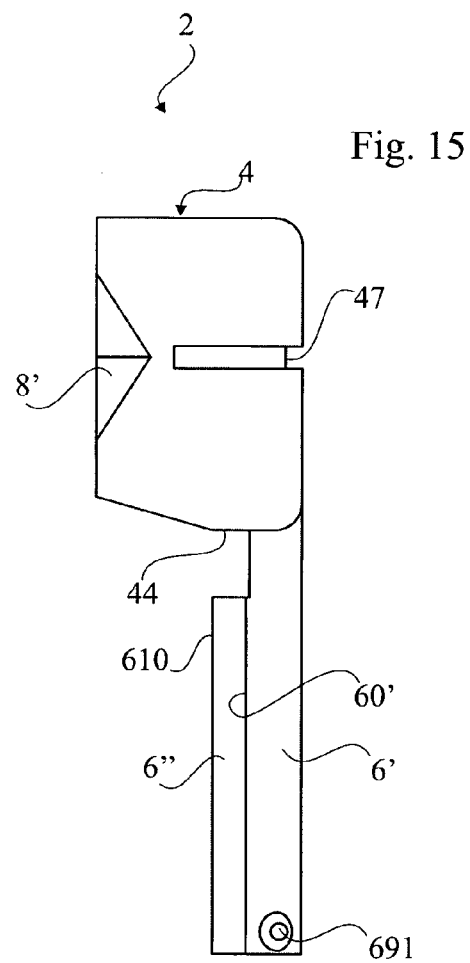
FIG. 15 is a side view of the female device of FIG. 14.

In FIGS. 14, 15 and 16, there is shown a female device 2 of an adapter adapted to interact with a male device as shown in FIGS. 11-13. As is evident, the holding part 6 of the female device 2 is designed in exactly the same manner as the male device 1. As a consequence the legs 6', 6" shown in the female device will present a minor image of the legs 5', 5" of the male device 1.

Figure 17:
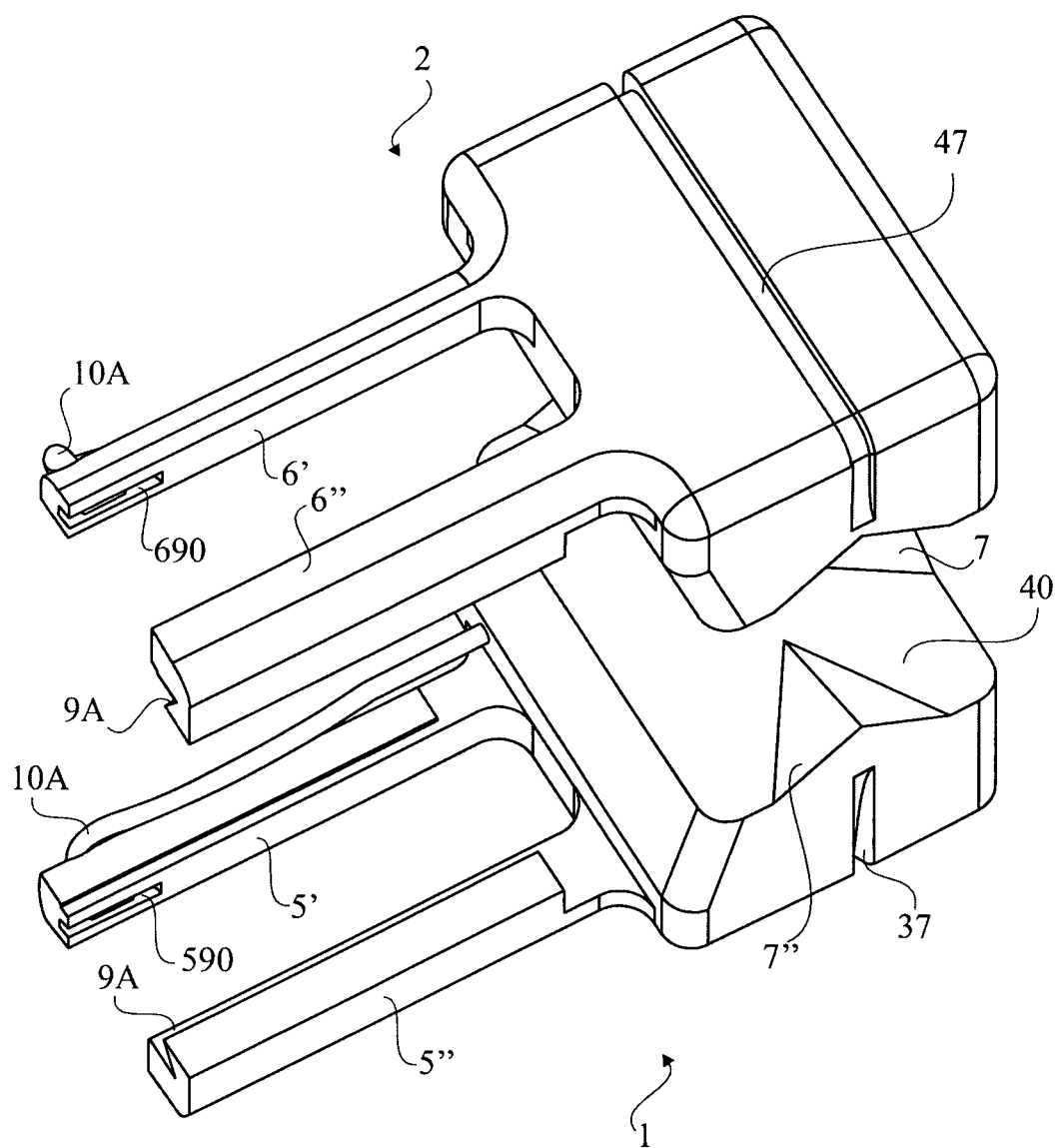
FIG. 17 is a perspective view of the male and the female devices according to the embodiments shown in FIGS. 11-16, in a dissembled mode, according to an embodiment.
Figure 18:
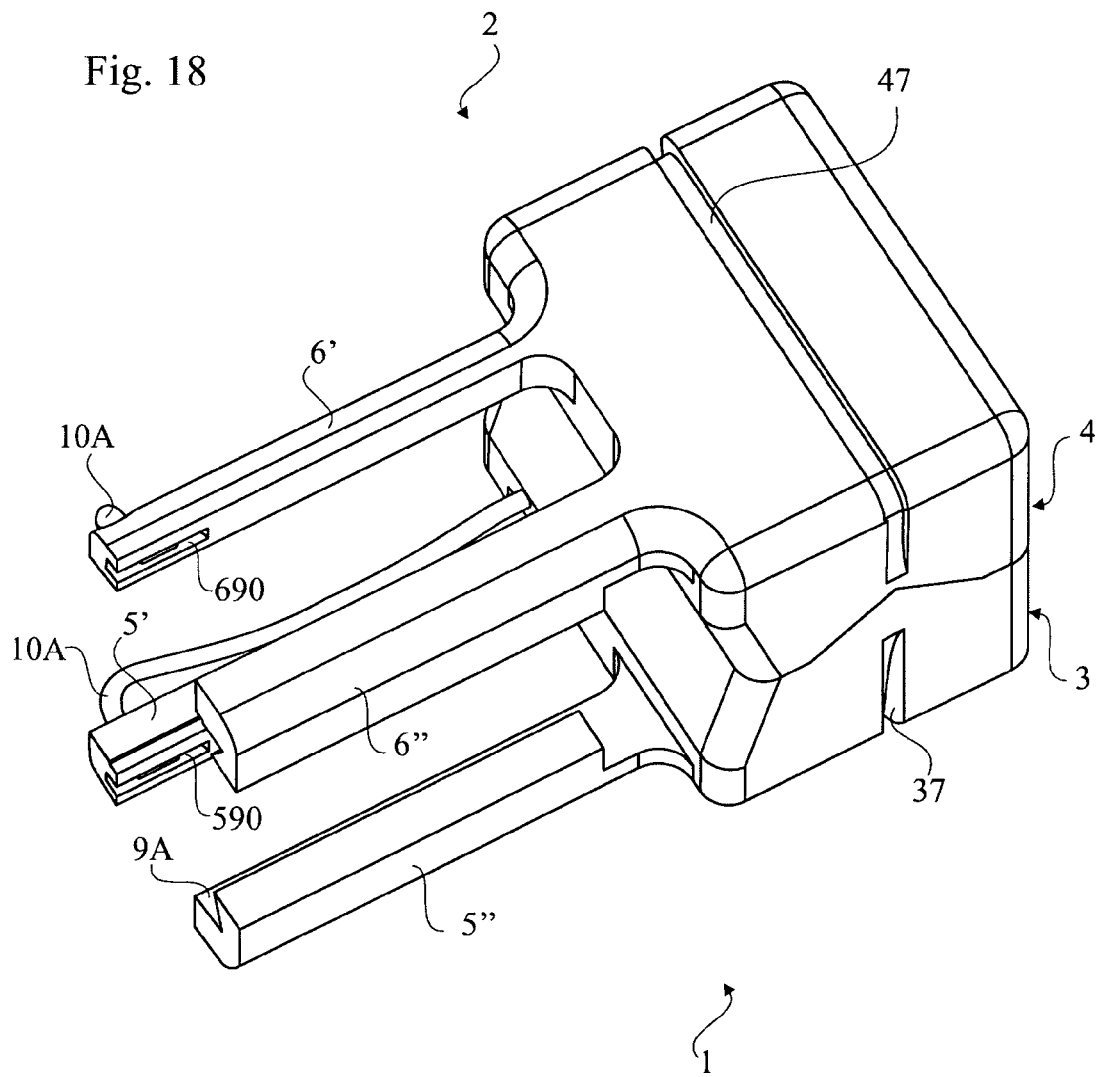
FIG. 18 is a perspective view of the male and the female devices shown in FIG. 17, in an assembled mode, according to an embodiment.

In FIGS. 17 and 18, the embodiments presented in FIGS. 11-16 are shown in dissembled and assembled mode respectively. The principle of interaction is exactly the same as already has been described in relation to FIG. 1 and will therefore not be described more in detail.

A further difference is the form of the notch 37, 47 that is provided for any suitable kind of retaining device (e.g. rubber band). Here, the notch 37, 47 is formed all the way at the back surface of both the male and female devices 1, 2.

The inventions are not limited by the examples/embodiments described above but may be varied within the scope of the appended claims. For instance, it is evident for the skilled person that the positioning and number of discrete elements may vary. It is also evident that the reference surfaces 30, 40 may vary in shape, e.g. to be inclined in relation to the central plane P2, and/or to have parts, or the whole, thereof curved, and/or having holes and/or indentations (evenly disposed) therein, etc.

Moreover, it is evident that in some applications it may be desired to have some of the "steering functions" of the male/female devices integrated into a ridge that extends across the whole width (or substantial part thereof) of the positioning device 3, 4. A further aspect where the skilled person realizes that many modifications are possible relates to the choice of material for the different parts of the articulator and also the model halves.

For instance, if a concept is used where the same articulator may be used over and over again (interchangeable model halves) a kind of material is beneficially used that provides for high wear resistance, preferably in combination with low friction. Of course, the properties of the surface may be achieved by appropriate coating. Hence, both different kind of metals and also plastic materials may be used to obtain different properties.

Moreover, it is evident that the exact configuration of the articulator may vary widely in relation to the configuration shown in the preferred embodiments, and still fulfilling the basic functional principles in accordance with the inventions. Moreover, in most cases two models 15, 16 are seen as sufficient, however, in some cases it may be beneficial to supply three models (not shown) wherein two of them are in accordance with above, but a "recess" is arranged into the third model, which model includes the dental preparation and wherein said "recess" provides for removal of some soft tissue from the model to be able to better see the exact inter fit of the dental restoration.

Finally, it should be understood that some aspects of the subject matter may be made the subject for separate, divisional applications to safeguard protection per se for such aspects, e.g. the use of a void inside of the dental models (and or the articulators) is one example of such an aspect that may be claimed individually.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

The invention claimed is:

1. An articulator, comprising:
an upper portion and a lower portion,
said upper portion including a first holding part arranged to hold a model of at least a part of an upper dental structure and including a first positioning device,
said lower portion including a second holding part arranged to hold a model of at least a part of a lower dental structure and including a second positioning device,
said first and second positioning devices enabling adequate positioning of and movability of said models to test the interfit therebetween, by means of having surfaces of said first and second positioning devices in direct contact with each other and further at least one male/female device having at least one element that protrudes from, or near, one of said surfaces and a corresponding recess near or in the other one of said surfaces, wherein said male/female device is in the form of at least two, preferably at least three, separate, discrete elements arranged near or in said surfaces, wherein said upper and lower portion are formed from free form fabrication and in wherein the first and second positioning devices are configured such that when said first and second positioning devices are engaged with each other said upper portion and said lower portion are in a position corresponding to a digital registered position of said upper and lower portion of a dental model; wherein the size and position of said discrete elements and recesses, respectively, are arranged to form a gap that is in the range 0-1 mm, preferably less than 0.5 mm, between side walls of each one of said elements recesses, respectively, when said surfaces are in contact.

2. An articulator according to claim 1, wherein the width (W) of the positioning device adjacent a transition zone between the positioning device and the holding part, is wider than the width (w) of the holding part.

3. An articulator according to claim 2, wherein 1.2 w<W<5 w to provide for at least one area that is accessible via the backside at a side wall of the positioning device facing in the same direction as the extension of the holding part.

4. An articulator according to claim 2, wherein (W) is in the range of 20-50 mm and/or w is in the range of 15-40 mm.

5. An articulator, comprising:
an upper portion and a lower portion,
said upper portion including a first holding part arranged to hold a model of at least a part of an upper dental structure and including a first positioning device,
said lower portion including a second holding part arranged to hold a model of at least a part of a lower dental structure and including a second positioning device,
said first and second positioning devices enabling adequate positioning of and movability of said models to test the interfit therebetween, by means of having surfaces of said first and second positioning devices in direct contact with each other and further at least one male/female device having at least one element that protrudes from, or near, one of said surfaces and a corresponding recess near or in the other one of said surfaces, wherein said male/female device is in the form of at least two, preferably at least three, separate, discrete elements arranged near or in said surfaces, wherein said upper and lower portion are formed from free form fabrication and in wherein the first and second positioning devices are configured such that when said first and second positioning devices are engaged with each other said upper portion and said lower portion are in a position corresponding to a digital registered position of said upper and lower portion of a dental model; wherein the size and position of said discrete elements and recesses, respectively, are arranged gap, wherein said gap extends continuously within a sector larger than 90° in any one of a parallel plane that crosses an element and a recess respectively when said surfaces are in contact.

6. An articulator, according to claim 1, characterized in that at least one, preferably both, of said holding parts is formed by two leg portions creating an open space between the leg portions.

7. An articulator, comprising:
an upper portion and a lower portion,
said upper portion including a first holding part arranged with a first interface to hold a model of at least a part of an upper dental structure and including a first positioning device,
said lower portion including a second holding part arranged with a second interface to hold a model of at least a part of a lower dental structure and including a second positioning device,
said first and second positioning devices enabling adequate positioning of and movability of said models to test the interfit therebetween by means of having surfaces of said first and second positioning devices in direct contact with each other and further at least one male/female device having at least one element that protrudes from, or near, one of said surfaces and a corresponding recess near or in the other one of said surfaces wherein the first and second positioning devices include dimensions which record the registered position of the upper and lower portion; wherein the size and position of said surfaces of said first and second positioning devices are arranged to forms a gap that is in the range of that is in the range 0-1 mm, preferably less than 0.5 mm between side walls respectively, when said surfaces are in contact, wherein the width (W) of the positioning device adjacent the transition zone between the positioning device and the holding part, is substantially wider than the width (w) of the holding part, wherein preferably 1.2 w<W<5 w, to provide for at least one area that is accessible via the backside at that wall of the positioning device facing in the same direction as the extension of the holding part.

8. An articulator according to claim 7, wherein said holding part is positioned substantially centrally in relation to the positioning device to provide two areas at said wall of the positioning device.

9. An articulator according to claim 7, wherein at least one of said interfaces includes an engagement arrangement arranged to releasably hold one of said models.

10. An articulator according to claim 7, wherein said engagement arrangement is arranged to enable snap-fitting.

11. Articulator according to claim 7, wherein said engagement arrangement includes a reference plane arranged to enable slide fitting.

12. An articulator, according to claim 7, characterized in that at least one, preferably both, of said holding parts is formed by two leg portions creating an open space between the leg portions.

13. An articulator in combination with a model of at least a part of a lower dental structure, said combination comprising:
an upper portion and a lower portion,
said upper portion including a first positioning device and including a first holding part arranged with a first interface to hold a model of at least a part of an upper dental structure having a corresponding interface and,
said lower portion including a second positioning device and including a second holding part arranged with a second interface to hold a model of at least a part of a lower dental structure having a corresponding interface,
said first and second positioning devices enabling adequate positioning of and movability of said dental casts to test the interfit them between by means of having surfaces of said first and second positioning devices in direct contact with each other and further at least one male/female device having at least one element that protrudes from, or near, one of said surfaces and a corresponding recess near or in the other one of said surfaces,
wherein at least one of said interfaces is made by free form fabrication and said interfaces include dimensions corresponding to a stored digital record of the design of the articulator;
wherein the size and position of said surfaces of said first and second positioning devices, respectively, are arranged to form a gap, wherein said gap extends continuously within a sector lamer than 90° in an one of a parallel lane that crosses an element and a recess respectively when said surfaces are in contact.

14. A combination according to claim 13, wherein at least one of said interfaces includes an engagement arrangement arranged to releasably hold one of said models.

15. A combination according to claim 14, wherein said engagement arrangement is arranged to enable snap-fitting.

16. A combination according to claim 14, wherein said engagement arrangement includes a reference plane arranged to enable slide fitting.

17. A combination according to claim 13, wherein at least one of said corresponding interfaces are integrated to form an integrated unit of at least one articulator and model.

18. A combination according to claim 13, characterized in that at least one, preferably both, of said holding parts is formed by two leg portions creating an open space between the leg portions.

19. A method of producing an articulator according to claim 1, further comprising providing the male/female device in the form of at least two, preferably at least three, separate, discrete elements arranged near or in said surfaces.

20. A method of producing an articulator according to claim 1, further comprising providing a width (W) of the positioning device adjacent the transition zone that is wider than the width (w) of the holding part, wherein preferably 1.2 w<W<5 w.

21. A method of producing an articulator according to claim 1, wherein manufacturing is achieved by means of free form fabrication.

* * * * *

UNITED STATES PATENT AND TRADEMARK OFFICE
CERTIFICATE OF CORRECTION

PATENT NO.        : 8,500,448 B2                                      Page 1 of 1
APPLICATION NO.   : 12/447455
DATED             : August 6, 2013
INVENTOR(S)       : Karlsson et al.

It is certified that error appears in the above-identified patent and that said Letters Patent is hereby corrected as shown below:

In the Specification

In column 6 at line 43, Change "I'" to --1'--.

In column 9 at line 5, Change "1)" to --1).--.

In column 12 at line 32, Change "with" to --width--.

In column 13 at line 3, Change "minor" to --mirror--.

In the Claims

In column 14 at line 51, In Claim 4, change "claim 2," to --claim 3,--.

In column 15 at line 14, In Claim 5, change "arranged" to --arranged to form a--.

In column 15 at line 45, In Claim 7, change "forms" to --form--.

In column 15 at lines 45-46, In Claim 7, after "of" delete "that is in the range".

In column 15 at line 46, In Claim 7, change "0.5 mm" to --0.5 mm,--.

In column 15 at line 53, In Claim 7, change "at that wall" to --at a side wall--.

In column 15 at line 57, In Claim 8, change "said" to --side--.

In column 16 at line 33, In Claim 13, change "lamer" to --larger--.

In column 16 at line 33, In Claim 13, change "an" to --any--.

In column 16 at line 34, In Claim 13, change "lane" to --plane--.

Signed and Sealed this
Fifth Day of August, 2014

Michelle K. Lee
*Deputy Director of the United States Patent and Trademark Office*